(12) United States Patent
Connelly et al.

(10) Patent No.: US 7,674,632 B1
(45) Date of Patent: Mar. 9, 2010

(54) METHOD AND COMPOSITION FOR HOMOGENEOUS MULTIPLEXED MICROPARTICLE-BASED ASSAY

(75) Inventors: Mark Carle Connelly, Doylestown, PA (US); Mark Kopnitsky, Easton, PA (US)

(73) Assignee: Zeus Scientific, Inc, Branchburg, NJ (US)

( * ) Notice: Subject to any disclaimer, the term of this patent is extended or adjusted under 35 U.S.C. 154(b) by 2040 days.

(21) Appl. No.: 10/295,118

(22) Filed: Nov. 15, 2002

Related U.S. Application Data

(60) Provisional application No. 60/340,039, filed on Dec. 10, 2001.

(51) Int. Cl.
*G01N 33/553* (2006.01)
*G01N 33/53* (2006.01)

(52) U.S. Cl. .................. 436/525; 436/518; 436/526; 436/8; 435/7.2; 435/7.7; 435/7.8

(58) Field of Classification Search .................. 436/525, 436/518, 526, 8; 435/7.2, 7.7, 7.8
See application file for complete search history.

(56) References Cited

U.S. PATENT DOCUMENTS

| | | | |
|---|---|---|---|
| 4,163,779 A * | 8/1979 | Harte et al. .................. 436/525 |
| 4,493,899 A | 1/1985 | Smith et al. |
| 4,690,905 A | 9/1987 | Diamond |
| RE32,696 E | 6/1988 | Schuurs et al. |
| 4,868,104 A | 9/1989 | Kurn et al. |
| 5,028,545 A | 7/1991 | Soini |
| 5,104,791 A | 4/1992 | Abbott et al. |
| 5,443,952 A | 8/1995 | Pestronk |
| 5,484,703 A | 1/1996 | Raben et al. |
| 5,567,627 A | 10/1996 | Lehnen |
| 5,573,911 A | 11/1996 | Victor et al. |
| 5,599,538 A | 2/1997 | Paul et al. |
| 5,663,066 A | 9/1997 | Raben et al. |
| 5,736,330 A | 4/1998 | Fulton |
| 5,776,487 A | 7/1998 | Wilson et al. |
| 5,780,319 A | 7/1998 | Wilson et al. |
| 5,981,180 A | 11/1999 | Chandler et al. |
| 6,057,107 A | 5/2000 | Fulton |
| 6,107,047 A | 8/2000 | Fledelius et al. |
| 6,117,646 A | 9/2000 | Qvist et al. |
| 6,121,004 A | 9/2000 | Pestronk |
| 6,127,113 A | 10/2000 | Atkinson et al. |

(Continued)

*Primary Examiner*—Mark L Shibuya
*Assistant Examiner*—Pensee T Do
(74) *Attorney, Agent, or Firm*—Joseph F Aceto, Esq.; James L. Wilcox, Esq.

(57) ABSTRACT

A method and composition for detecting and measuring analytes, such as antibodies, which are capable of binding with certain binding partners such as antigens. A homogenous assay is performed in the presence of free unbound antibodies. Such a homogeneous assay testing for specific antibodies is herein possible by defining of test subsets of microparticles having specific antigens thereon which are capable of binding with specific target antibodies. The microparticle suspension also includes at least two calibration subsets of microparticles having a binding partner thereon with at least two known levels of concentration which is capable of binding with human antibodies for the purpose of assay calibration. A verification subset of microparticles is included with another binding partner thereon at a known concentration, capable of binding with anti-human antibodies. This suspension is incubated with a human sample and then is incubated with a tagging component.

23 Claims, 6 Drawing Sheets

Active Calibration - Homogeneous Immunoassay for Human-IgG

U.S. PATENT DOCUMENTS

| | | |
|---|---|---|
| 6,150,113 A | 11/2000 | Decker et al. |
| 6,156,179 A | 12/2000 | Binder et al. |
| 6,159,699 A | 12/2000 | Brown et al. |
| 6,159,748 A | 12/2000 | Hechinger |
| 6,172,197 B1 | 1/2001 | McCafferty et al. |
| 6,696,304 B1 * | 2/2004 | Davies ........................ 436/518 |

* cited by examiner

FIGURE 2  Median Fluorescence of Active Calibrators

| Sample ID | Cal 1 – 12 IU | Cal 2 – 94 IU | Cal 3 – 266 IU | Verifier – 36 IU |
|---|---|---|---|---|
| 1 | 80 | 405 | 1342 | 173 |
| 2 | 87 | 423 | 1315 | 170 |
| 3 | 73 | 397 | 1310 | 177 |
| 4 | 106 | 634 | 2612 | 294 |
| 5 | 92 | 489 | 1590 | 163 |
| 7 | 70 | 568 | 1940 | 171 |
| 9 | 118 | 958 | 2830 | 375 |
| 10 | 192 | 1090 | 3566 | 662 |
| 11 | 148 | 980 | 3343 | 300 |
| 13 | 66 | 410 | 1322 | 157 |
| 14 | 106 | 514 | 1706 | 191 |
| 15 | 68 | 347 | 1172 | 109 |
| 16 | 78 | 707 | 2550 | 181 |
| 17 | 71 | 413 | 1403 | 147 |
| 19 | 352 | 2522 | 6877 | 1142 |
| 20 | 261 | 2187 | 6072 | 1165 |
| 21 | 366 | 2358 | 5633 | 998 |
| 22 | 398 | 2376 | 4684 | 697 |
| 24 | 122 | 681 | 1819 | 299 |
| 25 | 129 | 759 | 2536 | 259 |
| 26 | 49 | 386 | 1364 | 152 |
| 28 | 129 | 781 | 2190 | 230 |
| 29 | 254 | 1849 | 5322 | 847 |
| 30 | 299 | 2025 | 5668 | 1030 |

FIGURE 3 Slope, Intercept and $r^2$ Analysis of Calibration Curves

| Sample ID | Slope | Intercept | Corr. Coeff. $r^2$ |
|---|---|---|---|
| 1 | 5.0 | -16 | 0.99 |
| 2 | 4.9 | 2.4 | 1.00 |
| 3 | 4.9 | -19 | 1.00 |
| 4 | 10.1 | -136.6 | 0.98 |
| 5 | 6.0 | -16.9 | 1.00 |
| 7 | 7.5 | -65.0 | 1.00 |
| 9 | 10.7 | -26.1 | 1.00 |
| 10 | 13.5 | -52.5 | 1.00 |
| 11 | 12.8 | -91.5 | 0.99 |
| 13 | 5.0 | -20.7 | 1.00 |
| 14 | 6.4 | -17.9 | 0.99 |
| 15 | 4.4 | -18.4 | 0.99 |
| 16 | 9.9 | -113.5 | 0.99 |
| 17 | 5.3 | -31.2 | 0.99 |
| 19 | 25.6 | 71.8 | 1.00 |
| 20 | 22.8 | 8.8 | 1.00 |
| 21 | 20.5 | 246.3 | 1.00 |
| 22 | 16.4 | 458.6 | 0.98 |
| 24 | 6.7 | 46.8 | 1.00 |
| 25 | 9.6 | -49.6 | 1.00 |
| 26 | 5.3 | -52.0 | 0.99 |
| 28 | 8.1 | 25.2 | 1.00 |
| 29 | 20.0 | -3.5 | 1.00 |
| 30 | 21.1 | 42.3 | 1.00 |

FIGURE 4   Calibration Verification and Value Ratios

| Sample ID | Fluorescence | Observed | Value Ratio |
|---|---|---|---|
| 1 | 173 | 37.5 | 0.96 |
| 2 | 170 | 34.31 | 1.05 |
| 3 | 177 | 39.71 | 0.91 |
| 4 | 294 | 42.53 | 0.85 |
| 5 | 163 | 30.13 | 1.19 |
| 7 | 171 | 31.59 | 1.14 |
| 9 | 375 | 37.41 | 0.96 |
| 10 | 662 | 53.07 | 0.68 |
| 11 | 300 | 30.65 | 1.17 |
| 13 | 157 | 35.55 | 1.01 |
| 14 | 191 | 32.66 | 1.10 |
| 15 | 109 | 28.85 | 1.25 |
| 16 | 181 | 29.80 | 1.21 |
| 17 | 147 | 33.38 | 1.08 |
| 19 | 1142 | 41.75 | 0.86 |
| 20 | 1165 | 50.63 | 0.71 |
| 21 | 998 | 36.7 | 0.98 |
| 22 | 697 | 14.58 | 2.47 |
| 24 | 299 | 37.80 | 0.95 |
| 25 | 259 | 32.08 | 1.12 |
| 26 | 152 | 38.83 | 0.93 |
| 28 | 230 | 25.14 | 1.43 |
| 29 | 847 | 42.52 | 0.85 |
| 30 | 1030 | 46.69 | 0.77 |

FIGURE 5    Inclusion of the Value Ratio for Improve Accuracy

| Sample Dilution | Slope | Int. | Verifier | Value Ratio | Anti-DNA Before VR Adjust | Anti-DNA After VR Adjust | Anti-RNP Before VR Adjust | Anti-RNP After VR Adjust |
|---|---|---|---|---|---|---|---|---|
| Neat | 16.4 | 48.0 | 30.71 | 1.17 | 167 | 195 | 119 | 139 |
| 1:2 | 23.4 | 174.8 | 43.48 | 0.83 | 114 | 95 | 84 | 70 |
| 1:4 | 30.2 | 340.5 | 41.04 | 0.88 | 51 | 45 | 37 | 34 |

FIGURE 6    Determination of Cut-Off Values Between Positive and Negative Samples

| Sample Dilution | Anti-DNA FI | Anti-RNP FI | Anti-DNA After VR Adjust | Anti-RNP After VR Adjust | Anti-DNA Interpretation | Anti-RNP Interpretation |
|---|---|---|---|---|---|---|
| Neat | 2966 | 1957 | 195 | 139 | Positive | Positive |
| 1:2 | 3052 | 2110 | 95 | 70 | Borderline or Negative | Negative |
| 1:4 | 1983 | 1474 | 45 | 34 | Negative | Negative |

FIGURE 7 Detecting the Absence of Appropriate Sample.

| Sample Added | Slope | Intercept | $r^2$ | Verifier | Verifier Ratio |
|---|---|---|---|---|---|
| Yes | 13.7 | -42.6 | 1.00 | 36.33 | 0.99 |
| Yes | 13.5 | 36.0 | 1.00 | 25.32 | 1.42 |
| Yes | 11.8 | -16.8 | 1.00 | 31.47 | 1.14 |
| Yes | 6.9 | -32.5 | 0.99 | 32.61 | 1.10 |
| No | 2.0 | 6.8 | 0.95 | 213.64 | 0.17 |
| No | 0.8 | 39.5 | 0.97 | 475.16 | 0.08 |
| No | 0.4 | 53.8 | 0.82 | 940.43 | 0.04 |
| No | 0.3 | 41.0 | 0.58 | 1169.16 | 0.03 |
| No | 0.2 | 76.1 | 0.73 | 1469.65 | 0.02 |
| No | 0.5 | 65.9 | 0.74 | 774.19 | 0.05 |
| No | 0.4 | 43.0 | 0.7 | 959.52 | 0.04 |
| No | 0.3 | 60.6 | 0.8 | 1237.82 | 0.03 |
| No | 1.0 | 55.4 | 0.91 | 376.19 | 0.10 |
| No | 0.5 | 53.2 | 0.77 | 514.31 | 0.07 |
| No | 0.3 | 77.7 | 0.50 | 1358.65 | 0.03 |
| No | 1.0 | 54.1 | 0.94 | 348.29 | 0.10 |
| No | 0.4 | 67.7 | 0.69 | 935.71 | 0.04 |
| No | 0.4 | 72.8 | 0.79 | 942.18 | 0.04 |
| No | 0.6 | 40.8 | 0.90 | 667.47 | 0.05 |
| No | 0.5 | 63.2 | 0.78 | 620.22 | 0.06 |
| No | 0.5 | 52.9 | 0.83 | 713.67 | 0.05 |
| No | 0.5 | 46.7 | 0.85 | 660.85 | 0.05 |
| No | 0.4 | 62.2 | 0.66 | 1192.82 | 0.03 |
| No | 0.6 | 42.9 | 0.89 | 663.37 | 0.05 |

METHOD AND COMPOSITION FOR HOMOGENEOUS MULTIPLEXED MICROPARTICLE-BASED ASSAY

This application claims priority of U.S. Provisional Patent Application No. 60/340,039 filed Dec. 10, 2001 on "Quantitative Measurement Of Bound Analytes In The Presence Of Unbound Analytes With Enhanced Signal To Noise In A Homogeneous Assay Format", inventors Mark Carle Connelly and Mark Kopnitsky, assigned to Zeus Scientific, Inc. of Raritan, N.J. and currently pending.

BACKGROUND OF THE INVENTION

1. Field of the Invention

There are two main classifications of assays for the purpose of detecting and quantifying the presence of a molecule or type of molecule within an sample, namely, a heterogenous assay and a homogeneous assay.

The heterogeneous assay requires separation, either by washing or other physical means, of the reaction elements between the individual steps of the assay procedure. During an assay normally, a sample, such as a human serum sample, is initially brought into contact with the first analytical element of the assay by mixing or other means of being brought into contact therewith. This step can include some manner of incubation. Binding will occur between binding partners found in the sample which are associated with specific binding partners included in the first analytical element of the assay. This first analytical element is thereafter washed in order to become free of the unbound molecules of original sample and any unbound materials. The remaining portion of the assay including the first analytical element with material bound thereto is thereafter contacted with subsequent analytical elements of the assay. Additional processing steps can be included possibly including further washing or separating.

These wash or separation steps may be accomplished many ways such as by washing a coated well, magnetic particle separations, column chromatography, density separation or other types of steps. Normally, heterogeneous assays are used when high sensitivity and high assay precision are required. To achieve the desired sensitivity and precision, the reaction elements can be added in extremely excessive quantities. These reaction elements must be removed before subsequent analytical or processing elements are introduced.

Two molecules that can bind with respect to one another due to their mutual shapes or biologic activities are often referred to as a binding pair. Such a binding pair are usually described as being specifically associated with one another. These molecules actually fit together or attach as does a lock and key. Examples of such molecules are antibodies and the associated antigen with which each antibody specifically reacts. Other examples of binding pairs include receptors and the related hormones, cytokines, transmitters etc., complementary strands of DNA and enzymes and their substrates.

Each of the molecules that make up a binding pair are described as a binding partner. For example, an antibody not yet attached to its specific antigen is a binding partner and the specific antigen not yet attached is also defined as a binding partner. Another example of a binding partner includes single stranded DNA not hybridized to its complementary sequence.

2. Description of the Prior Art

Many compositions and methods have been patented for assaying for the purpose of determining the presence and quantity of a substance within a sample. Many of these patents are for the purpose of determining the presence of specific molecules such as antibodies within human serum samples.

The calibration of such assays has heretofore been deemed extremely difficult, especially for those assays which are homogeneous. The present invention provides a unique method for providing a dynamic and continuous calibration process for each individual human serum sample being tested wherein the calibration occurs at approximately the same time as the basic assay analysis. Also a customized calibration is provided for each distinct sample being analyzed rather than one single calibration for a multiplicity of sample tests that may be completely separate and distinct from one another except for the fact they may be testing in the same multi-well diagnostic tray.

Many patents have been granted for detecting and quantitatively measuring analytes in homogeneous and/or heterogeneous assays such as U.S. Pat. No. 4,493,899 patented Jan. 15, 1985 to L. Smith et al and assigned to City of Hope on a "Method Of Testing For Particular Antibodies In The Serum Of A Patient"; and U.S. Pat. No. 4,690,905 patented Sep. 1, 1987 to B. Diamond and assigned to Albert Einstein College of Medicine of Yeshiva University, a division of Yeshiva University on a "Method For Removal of Human Antibodies to Native DNA From Serum"; and U.S. Reissue Pat. No. Re. 32,696 patented Jun. 14, 1988 to A. Schuurs et al and assigned to Akzona Incorporated on an "Enzymatic Immunological Method For Determination Of Antigens And Antibodies"; and U.S. Pat. No. 4,868,104 patented Sep. 19, 1989 to N. Kurn et al and assigned to Syntex (U.S.A.) Inc. on a "Homogeneous Assay For Specific Polynucleotides"; and U.S. Pat. No. 5,028,545 patented Jul. 2, 1991 to E. Soiki and assigned to Wallac OY on a "Biospecific Multianalyte Assay Method"; and U.S. Pat. No. 5,104,791 patented Apr. 14, 1992 to S. Abbott et al and assigned to E.I. Du Pont de Nemours and Company on "Particle Counting Nucleic Acid Hybridization Assays"; and U.S. Pat. No. 5,443,952 patented Aug. 22, 1995 to A. Pestronk and assigned to Washington University on "Autoantibodies And Their Targets In The Diagnosis Of Peripheral Neuropathies"; and U.S. Pat. No. 5,484,703 patented Jan. 16, 1996 to N. Raben et al and assigned to United States of America on an "Assay Using Recombinant Histidyl-Trna Synthetase"; and U.S. Pat. No. 5,567,627 patented Oct. 22, 1996 to B. Lehnen and assigned to Trans-Med Biotech, Incorporated on a "Method And Composition For The Simultaneous And Discrete Analysis of Multiple Analytes"; and U.S. Pat. No. 5,573,911 patented Nov. 12, 1996 to J. Victor et al and assigned to Lifecodes Corp. on "Methods And Materials For Detecting Autoimmune Antibodies"; and U.S. Pat. No. 5,599,538 patented Feb. 4, 1997 to S. Paul et al and assigned to Igen, Inc. on "Autoantibodies Which Enhance The Rate Of A Chemical Reaction"; and U.S. Pat. No. 5,663,066 patented Sep. 2, 1997 to N. Raben et al and assigned to The United States of America as represented by the Department of Health and Human Services and National Institutes of Health on an "Assay Using Recombinant Histidyl-Trna Synthetase"; and U.S. Pat. No. 5,736,330 patented Apr. 7, 1998 to R. Fulton and assigned to Luminex Corporation on a "Method And Compositions For Flow Cytometric Determination Of DNA Sequences"; and U.S. Pat. No. 5,776,487 patented Jul. 7, 1998 to N. Wilson et al and assigned to Pasteur Sanofi Diagnostics on "Liposome Reagents For Immunoassays"; and U.S. Pat. No. 5,780,319 patented Jul. 14, 1998 to N. Wilson et al and assigned to Pasteur Sanofi Diagnostics on "Immunoassays To Detect Antiphospnolipid Antibodies"; and U.S. Pat. No. 5,981,180 patented Nov. 9, 1999 to V. Chandler et al and assigned to Luminex Corporation on "Multiplexed Analysis Of Clinical Specimens Apparatus And Methods"; and U.S. Pat. No. 6,057,107 patented May 2, 2000 to R. Fulton and assigned to Luminex Corporation on "Methods And Compositions For Flow Cytometric Determination Of DNA Sequences"; and U.S. Pat. No. 6,107,047 patented Aug. 22, 2000 to C. Fledlius et al and assigned to Osteometer Biotech A/S on "Assaying Protein Fragments In Body Fluids"; and U.S. Pat. No. 6,117,646 patented Sep. 12, 2000 to P. Qvist et al and assigned to Osteometer Biotech A/S on "Assaying Protein Fragments In Body Fluids"; and U.S. Pat. No. 6,121,004 patented Sep. 19, 2000 to A. Pestronk and assigned to Washington University on "Autoantibodies And Their Targets In The Diagnosis Of Peripheral Neuropathies"; and U.S. Pat. No. 6,127,113 patented Oct. 3, 2000 to R. Atkinson et al and assigned to Obetech, LLC on "Viral Obesity Methods And Compositions"; and U.S. Pat. No. 6,150,113 patented Nov. 21, 2000 to R. Decker et al and assigned to Abbott Laboratories on a "Method For Increasing Specificity In Competitive Immunoassays"; and U.S. Pat. No. 6,156,179 patented Dec. 5, 2000 to S Binder et al and assigned to Bio-Rad Laboratories on "Computer Directed Identification Of Paraproteins"; and U.S. Pat. No. 6,159,699 patented Dec. 12, 2000 to R. Brown et al and assigned to Molecular Light Technology Limited on an "Enzyme Linked Chemiluminescent Assay"; and U.S. Pat. No. 6,159,748 patented to M. Hechinger on Dec. 12, 2000 and assigned to AffiniTech, LTD on an "Evaluation Of Autoimmune Diseases Using A Multiple Parameter Latex Bead Suspension And Flow Cytometry"; and U.S. Pat. No. 6,172,197 patented Jan. 9, 2001 to J. McCafferty et al and assigned to Medical Research Council and Cambridge Antibody Technology Limited on "Methods For Producing Members Of Specific Binding Pairs".

3. Definitions

Ag=Antigen, a material to which an antibody binds.
DNA or dsDNA=Deoxyribose Nucleic Acid, dsDNA represents double stranded DNA
ELISA=Enzyme Linked Immunosorbent Assay. An assay where a binding partner, such as an antibody, is coupled to an enzyme. The presence of antibody binding is detected by adding a substrate that, if present, is acted on by the attached enzyme and creates a detectable change in the substrate.
IFA=Immunofluorescent assay or Indirect Fluorescent Assay. An assay where a binding partner is coupled to a fluorescent compound. The presence of binding by the binding partner is detected by a heterogeneous process including washing out of unbound material, and then looking for fluorescent staining of a solid substrate such as cell or tissue section microscopically using a immunofluorescent microscope.
IgG=Immunoglobulin G. One of several classes of immunoglobulins or antibodies.
mL=Milliliter.
mg=milligram
PE=Phycoerythrin, a fluorescent phycobilliproten that may be used as a reporter molecule.
SLE=Systemic Lupus Erythematosis. A systemic autoimmune disease characterized by the presence of antibodies to "self" components such as DNA.

SUMMARY OF THE INVENTION

A homogeneous assay is performed quite differently from a heterogeneous assay since it is conducted without any separating steps, either by washing or other physical means. The washing steps normally required in a heterogenous assay which remove one or more of the reaction elements or which are performed before proceeding to subsequent analytical steps, are not required in a homogeneous assay. Typically, a sample to be assayed is initially contacted with the first analytical element of the assay. Other elements of the assay, if required, may either already be present with the first analytical element, or are subsequently added thereto. There is no separation step, or any attempt whatsoever to separate the bound and free portions of the sample prior to reading the assay. Homogeneous assays are typically used in those assays characterized by low to medium range sensitivity requirements.

Homogenous assays are generally more reliable than heterogenous assays since the possibility of human or instrument error is minimized by eliminating one or more washing or separation steps. However, homogeneous assays are more difficult to read and calibrate since the analyte must be evaluated in the presence of irrelevant components such as other molecules in the sample, unbound target molecules as well as free or unbound portions of the one or more analytical elements. Also, more particularly, bound analyte must be evaluated in the presence of similar unbound analyte.

The present invention makes use of a plurality of subsets of microparticles with various analytical elements physically conjugated thereon. These microparticles are often referred to as beads. They are often spherically shaped and thus, more particularly, are called "microspheres". These microparticles are commonly made of polystyrene or latex. The diameter of the beads normally range from nanometers to microns. Beads of many different sizes could be utilized, however, for the present invention a uniform bead diameter of 5.6 microns has been found to work very well. These beads are also separately identifiable in order to determine which individual beads are used for calibration or verification or for binding with analyte.

A reporter molecule is used for the purpose of facilitating detection of the presence of bound target molecules and also for achieving some level quantification of measurement thereof. These reporter molecules can be chosen from many classes of compounds however usually they comprise enzymes, or a fluorescent molecule such as fluorescein (FITC) or phycoerythrin, also commonly referred to as PE. In the preferred embodiment of the present invention, the reporter molecule of choice is PE. This preference is somewhat dictated by the design of the dedicated flow cytometer instrument being used in the examples shown hereafter, however other reporter molecules may be utilized as dictated by the equipment used, such as a reader, in performing the assay or by the type of assay being conducted.

A conjugated binding partner that creates a detectable signal in the assay is commonly referred to as a secondary reagent. The manner of conjugation may be covalent but the means of binding can certainly include many manners of binding other than being covalently bound. The present invention is particularly adapted for use with an anti-human immunoglobulin type-G antibody which is capable of covalently being attached to fluorescent compounds such as PE or fluorescein (FITC). Of course, other secondary reagents would be also be capable of use with the composition and method of the present invention for many purposes.

Homogeneous assays have many advantages over heterogeneous assays. They are easier to perform and easier to automate because they do not require washing or separation steps. Homogeneous assays can generally be performed more rapidly than heterogeneous assays. Also, the absence of any washing or separation steps greatly helps to eliminate the potential for human and other errors which can be introduced by inadequate performance of these operational steps. Ease of use for the operator and the increased simplicity of automating the processes of homogeneous assays makes this type of assay procedure highly desirable for simple, low cost, and rapid test systems.

Homogeneous assays are employed for many unique purposes such as when the presence and quantity of a substance is to be determined within a sample, and are particularly where the measured component is typically absent but can be used in many other applications also. An example would be the drug, Theophylline. The presence and concentration of this particular drug in the serum of a patient may be measured by several homogeneous assays. In any given patient sample, the drug is either there or not. There is no specific need to separate "bound Theophylline" from "free Theophylline" for the test system because the objective is to bind all of the Theophylline found present in the sample. Thus, one need only find a reporting procedure that will report, or will be inhibited from reporting, only when Theophylline is present, and will work appropriately in any type of sample whether it is a human serum sample, plasma sample, or other type.

Homogeneous assays are not typically utilized when the target reaction element of interest represents only a small proportion of the total amount of that element in the assay. One such reaction element of interest could be a specific target antibody. All human sera contain many antibodies of vastly different types. The total quantity of antibody, and the immunoglobulin classes present, will also vary appreciably from individual to individual. Serum Immunoglobulin type-G is usually the most prevalent, and is typically found at concentrations between 4 and 15 mg/mL in most human serum samples. The population of IgG antibody is composed of many identical IgG molecules. The different IgG molecules can be distinguished from one another by identification of the specific antigen to which they will bind. At any given time, the serum of a given person contains antibodies that react with tens of thousands of different antigens.

The present invention consists of two computational components working together with one essential and one preferred compositional component to enable a use of a homogeneous assay format.

An essential compositional element of the present invention is that each sample being analyzed is brought in contact with assay calibrators. This contact can result from mixing and can be further enhanced by incubation therewith. The assay calibrators of this invention are internal to the homogeneous sample test mixture, and they can be incubated in the sample mixture along with the testing components, under the same conditions, including, but not limited to, time, temperature, and light to which the whole assay is subjected. Preferably, the calibrators used are composed of the same class of unconjugated, non-signal generating binding partners as the signal generating binding partner or can be an unconjugated binding partner having the same binding properties as the conjugated binding partner. The calibrators should be arranged such as to have different, quantifiable levels of binding activity. Preferably three different calibrator subsets of microparticles will be utilized with each subset having a different concentration level of binding partner coated thereon.

These calibrators serve to determine the slope and intercept of the signal per unit value of the analyte of interest generated within the sample. This is a critical analytical aspect of the present invention because the slope will change substantially from sample to sample in a homogeneous assay because of the unique level of "unbound" analyte present that will dynamically compete or inhibit the signal generated by the analyte of interest. By using calibrators that are either the same as, or have the same binding properties as, the conjugated binding partner, factors that effect the level of binding of the conjugated binding partner, will equally effect the activity of the calibrators. The number of subsets of independently addressable internal calibrators must be at least one, more preferably, two and, most preferably, three or more.

As an example of this, in the present invention, the calibrators are composed of different quantities of Goat-anti-human-IgG bound to individually addressable microspheres. The conjugated binding partner can be any binding partner having the proper properties, however, for the present invention the conjugated binding partner is Goat-anti-human-IgG conjugated to phycoerythrin.

Another essential compositional element of the present invention is that each and every human serum sample being analyzed is brought in contact with one or more verifiers. This verifier component preferably is capable of verifying the calibration at the same time as detecting and measuring target analytes. It is preferred that there be no more than five calibration verifiers. No more than three verifiers is actually preferred, but the most highly preferred embodiment makes use of only one verifier. Each verifier will be associated with an identical separately identifiable multiplicity of verifier microparticles, normally as many as 1000 such microparticles. The calibration verifier is preferably internal to the homogeneous sample test mixture being analyzed, and is incubated simultaneously in the sample mixture along with the testing components and calibrators, under the same conditions, such as, but not limited to, time, temperature, and light to which the whole assay is subject. The calibration verifiers contain a known amount of a binding partner with which the conjugated binding partner reacts or can contain binding partner with the same binding properties as the specific binding partner targeted by the conjugated binding partner. The assay value of the calibration verifier is predetermined at the time of manufacture.

As an example of this, in the present invention, the calibration verifier is a quantity of human IgG bound to an independently addressable microparticle or bead, whereas the conjugated binding partner is Goat anti-Human Immunoglobulin type-G conjugated to phycoerythrin.

A method of reducing and analyzing the calibrators, and verifiers is included internal to each assay. The calibrators generate a unique, standard plotted line for each individual human sample analyzed. This is one of the distinct advantages of the homogeneous assay of the present invention because a separate unique calibration and verification is performed at the same time as the measurement for target analytes and in the same environment. Since the unbound tagging component is not washed or removed from a homogenous assay, the dynamic binding activity therewithin never conclusively ceases. As such, the calibration for each human specimen tends to change slightly or "drift" over time. These assays are normally performed in a 96 well assay plate with as many as 90 or more different human serum samples, each one located in a different well therein. On the other hand, with assays utilizing an external calibration system, three or more of these wells are utilized for determining the calibration used for all samples in the 96 well assay plate. However, with the internal calibration or well-specific calibration assays of the present invention, a separate calibration is performed in each well within each of the individual human serum samples being analyzed. Also, with the intra-well calibration system used in the assay of the present invention, those three or more wells which are used for calibration in an externally calibrated assay can now be made available for testing three additional human serum samples thereby increasing the output level of human serum tests performed per 96 well plate by at least three.

When performing the calibration using the preferred three calibration subsets of microparticles, the generation of a linear standard curve is anticipated. Mathematical transformation of the data may be performed in order to achieve this linear standard curve. It may be necessary to transform either the independent (X axis) or dependent (Y axis) variables, or both, in order to achieve a linear standard curve. The specifics of the required transformations will be determined by the assay properties and the linearity of the signal response generated.

After the calibration curve has been calculated, the value of the calibration verifier is determined from the internally generated standard curve. The apparent or derived value for the verifier is then compared, by means of a ratio, with the original known value for that verifier. The ratio of the observed to the known values for the verifier can be used as a correction factor to adjust all subsequent values derived from that standard curve. This fine tuning of the ratio of the observed to the known values will greatly enhance the accuracy of the detection and measurement of concentration levels of the target binding partners, such as the specific target antibodies. If the standard curve is not linear, two or more verifiers can be required to account for the more complex and changing shape of the curve. In the case of linear standard curves however, a single verifier has been found to be sufficient to adjust assay values derived from the standard curve. This corrective adjustment is achieved by calculating the number of units of analyte bound from the internal standard curve and multiplying that value by the ratio of the Known Verifier Value divided by the Observed or Apparent Verifier Value. In this way the slope of the signal per unit analyte is objectively measured in each sample analyzed, and the accuracy of the calibration and final determination verified.

As an example of this, in the present assay a sample contains antibody to dsDNA. The quantity of anti-dsDNA is determined by the fluorescent intensity of the response on a subset of microspheres or beads coated with dsDNA. The intensity of fluorescence is then converted into International Units (IU) of activity by use of the internal standard curve. If a verifier has an assigned value of 50 IU and an observed value of 55 IU and the patient sample has an observed value of 500 IU of anti-dsDNA, then the value of the dsDNA would be corrected or adjusted as follows:

50 IU divided by 55 IU=0.9090 [Calibration Verification Factor]

500 IU (observed)×0.9090=454.5 IU actual IU dsDNA

The quantitative value of anti-dsDNA reported in this assay would be 454.5, not 500 resulting in a more accurate calibration due to the correction factor generated by verification.

More generally, the conjugated binding partner that generates the detectable signal is a deliberate mixture of binding partner conjugated to the reporter and unconjugated "free" binding partner. In the example of a binding partner that is an anti-IgG antibody conjugated to a reporter, the free Immunoglobulin type-G antibody in the patient sample competes for and binds much, if not most, of the conjugated binding partner added to the assay. The addition of unconjugated anti-IgG, not bound to a reporter was expected to add still further competition to the assay. It was anticipated that the unconjugated anti-IgG would bind to the specifically bound IgG as well as the free IgG. Having bound the specifically bound IgG, it would then block the anti-IgG conjugated to the report and thereby reduce, not enhance, the signal generated by the assay system. Surprisingly, the opposite was observed. A marked increase in reporter signal was seen, without a significant increase in background binding or "noise".

It is an object of the method and composition of the present invention to provide a multiplexed microparticle-based homogeneous assay to be usable to detect within a sample the presence and approximate quantity of target analytes which are specifically capable of binding to particular binding partners with the assay performed in the presence of free unbound analyte.

It is an object of the method and composition of the present invention to provide a multiplexed microparticle-based homogeneous assay which makes use of a plurality of separate subsets of calibration microparticles for generating a unique calibration curve for each and every individual human sample being tested.

It is an object of the method and composition of the present invention to provide a multiplexed microparticle-based homogeneous assay which includes a verification subset of microparticles having a second binding partner thereon capable of verifying the calibration applied to each separate homogeneous assay applied to each separate sample.

It is an object of the method and composition of the present invention to provide a multiplexed microparticle-based homogeneous assay wherein a subset of microparticles will yield a verification or correction value which can be used to modify a calibration calculation to increase the accuracy of measurement of bound target analytes in the presence of unbound analytes.

It is an object of the method and composition to provide multiplexed microparticle-based homogeneous assays which can accurately determine when the assay has yielded results outside of a predetermined reliability range for determining whether the yielded result is sufficiently reliable to be reported.

It is an object of the method and composition of the present invention to provide a multiplexed microparticle-based homogeneous assay which can accurately measure bound analytes both quantitatively and semi-quantitatively in the presence of free unbound analytes.

BRIEF DESCRIPTION OF THE DRAWINGS

While the invention is particularly pointed out and distinctly claimed in the concluding portions herein, a preferred embodiment is set forth in the following detailed description which may be best understood when read in connection with the accompanying drawings, in which:

FIG. 2 is a table illustrating the data which generated the calibration curves shown in FIG. 1;

FIG. 3 is a table illustrating the slope, intercept and r-squared analysis of the calibration curves shown in FIG. 1;

FIG. 4 is a table illustrating the calibration verification and value ratios generated;

FIG. 5 is a table illustrated the use of a value ratio for correcting the calibration curve in order to yield improved accuracy in calibration;

FIG. 6 is a table showing the cut-off values between positive and negative samples for determining the reliability of the result; and FIG. 7 is a table showing the capability of the composition and method of the present invention in the detection of the absence of an appropriate sample within a given well.

DETAILED DESCRIPTION OF THE PREFERRED EMBODIMENT

Figure 1:
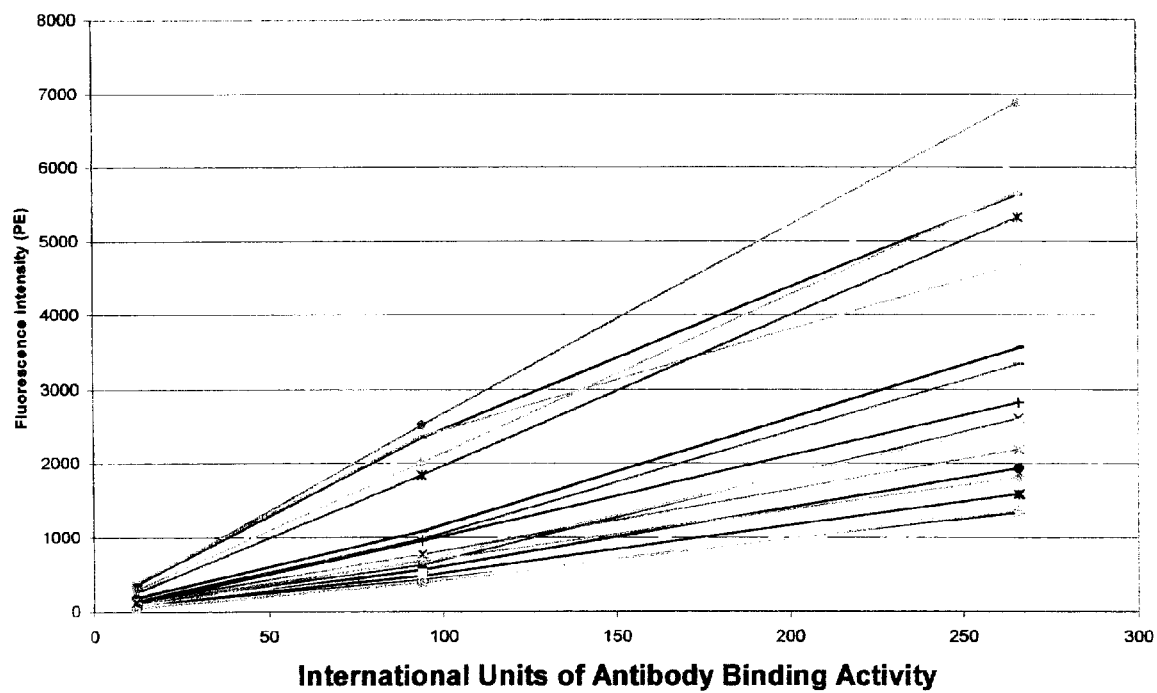
FIG. 1 is a graph showing the active calibration curves for each of a plurality of different human specimens used in a homogeneous immunoassay for human-IgG correlating fluorescence intensity with international units of antibody binding activity.

One embodiment of the present invention is particularly usable in the field of autoimmune disease diagnostics. In this field, it is important to detect and quantify the presence of certain antibodies which are known to have specificity against certain cellular antigens. One example of such an antigen, is dsDNA.

Approximately 80% of people diagnosed with the disease Systemic Lupus Erythematosus (SLE) are found to have antibody in their serum that react with dsDNA. The significance of this antibody in the pathogenesis of the disease is not understood completely. However, the presence of this specific antibody is an important diagnostic indicator when attempting to differentiate SLE from other closely related disorders. Typically IFA or ELISA, both heterogeneous assays, are used to measure this antibody. The assays are conducted by incubating the patient sample with either a fixed cell or dsDNA bound to a solid support. The cells, or solid support, are then washed to remove all the other IgG molecules that did not bind to dsDNA. Then a secondary reagent, typically but not exclusively an anti-IgG antibody, is incubated with the cells or solid support. This reagent is often linked to a reporter. If the patient sample does contain antibody to dsDNA, then the secondary reagent and its reporter molecule will bind to the cell or solid support via its binding to the anti-dsDNA IgG already there. If no anti-dsDNA was present in the patient sample, then no secondary reagent binds. Finally any excess secondary reagent must be washed away and the presence of the reporter molecule determined by appropriate means, such as immunofluorescence microscopy or the addition of a substrate (detection system). In these diagnostic tests, the need for high sensitivity or extreme precision is not the purpose behind the desire for use of a heterogeneous assay. These diagnostic tests are particularly adaptable for use with a heterogeneous assay because of the need to separate the Immunoglobulin type-G that binds dsDNA, from all the IgG in the patient sample that is specific for other antigens. It is likely that for almost any given antigen used in a specific assay, that the antigen-specific IgG represents only a small fraction of the total IgG present in the total sample. If separation of the irrelevant from the specific IgG does not occur, then the secondary reagent will bind to the free IgG in the patient sample. Because there is much more free IgG than specifically bound IgG in the sample, the signal to noise ratio would be considerably improved, that is considerably higher, if the free IgG were removed prior to measuring the presence of the reporter. There is also an equally important need to remove excess reporter. If the excess reporter is not removed, the signal generated would depend completely on the amount of secondary reagent added, regardless of whether specifically bound antibody had been present or not.

The presence of large quantities of free IgG that bind the secondary reagent and compete for binding to the specifically bound IgG of interest would seem to preclude accurate detection of bound IgG in a homogeneous assay format. Although large quantities of secondary reagent could be added to bind all the free IgG and still have sufficient secondary reagent remaining to bind the specifically bound IgG, this proves to be impractical and unworkable. It is impractical because so much secondary reagent is required that is becomes cost prohibitive. It is also unworkable, because even if the cost could be brought down to reasonable levels, the large quantity of secondary reagent leads to high background reactivity that obscures all but the most dramatic of the specific target binding. In addition, the amount of free IgG can vary widely over a broad range (4 to 15 mg/mL) meaning that the required quantity of extra secondary reagent will vary from individual to individual. A constant high concentration of secondary reagent has the disadvantage of possibly being a quantity, for someone whose IgG concentration level is at 6 mg/mL, that is in gross excess and leads to high backgrounds. On the other hand, the same amount may be insufficient for someone whose IgG concentration level is at 14 mg/mL.

The present invention, facilitates the use of a homogeneous assay format for the user to detect and, to some degree, quantify specifically bound IgG in the presence of free, unbound IgG. It is believed that the principles inherent to this invention are general in application thereof, and may therefore, be extended to other assays systems that seek to detect analytes other than IgG.

The present invention enables semi-quantitative measurement of a specific binding partner, even in the presence of a significant amount of excess free binding partner. This result is achieved through the use of a unique combination of internal calibrators in each and every sample that respond actively and dynamically to the conditions that exist within a patient sample in a manner that is indistinguishable to that of the target analytes. The accuracy and dynamic range of the assay are further enhanced by the ability to actively adjust the calibration curve for accuracy in view of the unpredictable microenvironment of clinical samples, and the ability to generate increased signal in the presence of significant quantities of "unbound" irrelevant but antigenically identical analyte.

Example 1

Active Calibration

In this embodiment of the present invention, a conjugate of Goat anti-human Immunoglobulin type-G (IgG) was coupled to PE to measure human antibody in patient samples that react with autoantigens. To calibrate the assay, individually identifiable microparticles were coated with Goat anti-human IgG. These microparticles were coated with different known concentration levels of antibody in order to achieve different levels of binding activity. Samples of human serum were incubated with a mixture of the microparticle beads that contained three subsets of calibrator beads in order to examine the effect of the free antibody on the slope and intercept of the mathematical algorithm curve representing the general relationship of the measured fluorescence intensity to the antibody binding activity.

Methods: Samples of whole human serum were diluted 1:200 in sample diluent. Ten microliters of diluted sample was incubated with 50 microliter of microsphere suspension containing three calibrator subsets of microparticles and one subset of calibration verifier microspheres. Each of the subsets included approximately 1000 microspheres. The binding capacity of the anti-human antibody positioned on the 1000 microparticle subset in each of the three calibrators were 12, 94, and 266 International Units (IU) respectively. The antibody positioned on the calibration verifier microspheres had a predetermined value of 36 IU. The patient samples and calibrators and verifiers were incubated together for 30 minutes at room temperature. At the end of the incubation time, 100 microliters of Goat anti-human IgG-PE was added to each well. The homogeneous assay suspension of sample and microspheres were incubated for an additional 30 minutes at room temperature, then read on a dedicated flow cytometer, namely a Luminex 100 instrument from Luminex Corporation, Austin, Tex. This instrument has the capability of detecting the presence of a single microparticle, and identifying which subset to which the microparticle belongs and, finally, determining the amount of tagging component bound thereto.

Results: The results of the raw fluorescence values for the calibrators and verifiers are shown in FIG. 2. Although the binding capacity of each of the calibrator microsphere populations is identical between patient samples, and even though the same conjugate was used in each sample, the level of fluorescence observed was markedly different between samples.

FIG. 1 graphically illustrates how "free IgG" and the microenvironment of each sample affects the observed fluorescence of the calibrators. FIG. 1 is a graphical representation of the calibration data shown in FIG. 2. Each linear plot generated by the three sets of calibration coordinates provides a calibration curve for each different patient serum sample. Note that there is a large difference in slope between the individual patient samples, even though the same calibrators and tagging conjugate was used in each sample. This difference in slope is due to the different concentrations of total IgG present in each of the patient samples that results in different amounts of binding to the calibrators, and different levels of conjugate binding to "free" or "unbound" IgG in the solution.

FIG. 3 indicates the results of the application of a linear regression analysis on each of the calibration curves. Each individual human serum sample results in a unique slope and intercept, however, the correlation coefficient of all curves was very close to 1 in all cases. This indicates the predicted curve in each case is highly associated with the variance within, and closely predicts the observed data, in spite of the obviously large differences in response between individual samples.

It is precisely this difference between samples that renders traditional modes of external calibration unusable for this homogenous system. Typically, calibrators are run separately from the patient samples being studied. Often they are performed using the same reagents, at the same time, and under the same conditions as the test samples. However, the calibration assumes that the response in each sample is the same as that in the calibration curve. That is, that the fluorescence per unit of analyte measured in the sample is the same as that for the calibrators. Therefore, a fluorescence of 4000 in the calibrator may represent 150 units of activity, and that level of fluorescence activity must represent 150 unit of activity for all of the different human samples. Often to make that assumption true, a heterogeneous assay must be used in order to eliminate the effect of competition by unbound analyte. As illustrated in FIGS. 1, 2 and 3, for the homogeneous assay of the present invention, the assumption of uniform response in all samples is not true. A fluorescence response of 4000 represents 150 units of activity in only 1 of the 24 samples tested. The use of separate individual internal, active calibrators give the assay procedure the ability to generate calibration curves that respond to the microenvironment of each distinct sample, and generate results which are to some extent quantitative.

The influence of the microenvironment within the sample on the quantitative interpretation of an analyte is further illustrated by the results generated by the verifier microsphere. The beads within the verifier subsets were each coated with a constant concentration level of human IgG and added to all samples. In the absence of competitive "free" or unbound analyte, the conjugate binding to this microsphere should be identical in all samples. As shown in FIG. 2, the fluorescence response ranged from 109 to 1165. Therefore, the level of fluorescence generated by a given, and constant amount of target analyte, differed by more than an order of magnitude in as few as these 24 samples.

Example 2

Calibration Verification and Value Ratio Adjustment

The inclusion of a verifier microsphere coated with an antibody at a known concentration provides a known amount of binding activity which provides a means of verifying the accuracy of the calibration. This verifier also provides a subsequent adjusting value to improve the overall accuracy of the initial calibration result. The fluorescence intensity measured for the verifier microsphere is shown in FIG. 2. FIG. 3 shows the results of a linear regression standard curve performed for the calibration microparticles of each sample.

Method: The general equation for a straight line curve in this calculation is $Y=mX+b$. Where Y is the fluorescence, m is the slope of the line, and B is the intercept with the Y-axis. The graph is drawn using the number of International Units of Binding Activity (IU) as the abscissa values and the fluorescence as the ordinate values. To determine the number of IU represented by a given observed fluorescence intensity, it is necessary to solve the general equation for X as shown in the below mathematically equivalent equation:

$$(Y-b)/m=X$$

For each fluorescence value observed for the verifier microsphere (FIG. 2), the number of IU was calculated in that sample using the slope and Y-intercept obtained on that sample (FIG. 3) and the equation above. The value obtained, was then compared by way of a ratio, to the known value at the time of manufacturing, using the formula:

Known Value/Observed value=Value Ratio (VR)

Results: FIG. 4 shows the values obtained. The known value for the verifier employed was 36 IU. Observed values ranged from a low of 14.58 to a high of 53.07. This was true even though the observed fluorescence varied by more than an order of magnitude. Further, note that the lowest and highest observed values for the verifier microspheres had remarkably similar fluorescence intensities (697 and 662 respectively). These samples did not have either the highest or lowest slopes obtained in this data set (see FIG. 3), although the low sample did have an unusually high Y-intercept value.

The Value Ratio provides a correction factor that may be used to make slight adjustments to the calibration curve that is originally determined by the measured fluorescence on the calibration microspheres. The value ratio will be able to adjust the calculated IU for other analytes measured in the same test sample. A sample was obtained from the World Health Organization (WHO) that is certified to contain 200 IU of anti-DNA antibody. The sample was tested "neat" without dilution, diluted 1:2 in phosphate buffered saline (PBS), and diluted 1:4 in PBS. Each neat or diluted sample was then diluted 1:200 and 10 microliters of sample was incubated with 50 microliters of multiplexed microsphere suspension containing at least 1000 microspheres each of three calibrators, a verifier microsphere, and microspheres coated with various cellular antigens capable of binding with target antibodies. The sample was incubated for 30 minutes at room temperature, and then 100 microliters of Goat anti-Human IgG-PE conjugate was added to all test samples.

The fluorescence intensity for each analyte in the samples was converted into IU by means of the internal standard curve as illustrated above. Then each result corrected by multiplication by the Value Ratio for that sample as shown below.

(IU obtained from internal curve)×Value Ratio=VR Adjusted Reportable IU

The sample was found to be positive for antibody to dsDNA and a nuclear antigen called RNP-A. FIG. 5 shows the results obtained with and without adjustment of the quantitative result using the Value Ratio.

FIG. 5 illustrates the improved accuracy obtained when the Value Ratio is factored into the calculation. The WHO standard that we used in this test is known to have a value of 200 IU when tested "neat". Active calibration alone gave a value of 167, but after employing the Value Ratio adjustment, a result of 195 was obtained.

Similar improved accuracy was also demonstrated when the sample was diluted 50% several times. Each dilution should give a value approximately half that of the previous value. The multiplication of the predicted value by the Value Ratio adjustment factor, yielded a calculated IU of anti-DNA in the sample in each dilution step that was closer to one half the previous value.

A target value for the anti-RNP-A antibody in this sample has not been established by the World Health Organization. FIG. 5, however, also shows that the value was more accurately half that of the previous dilution when the VR was employed in the calculation. The active calibration of the present invention corrected for the majority of sample effects, including overcoming a near doubling of the slope and a seven fold increase in intercept. However, accuracy was further improved by the inclusion of the VR adjustment factor. This improvement occurs because the microenvironment of the diluted sample is different than that of the undiluted sample. The calibrators adjust to accommodate for the change, but they are at best, only yielding estimates of the "true" curve. Therefore, due to errors in the measurements of the individual calibrator values, the least squares best fit through the data, may not actually provide the "true" fit through the data. The VR serves to bring the least squares fit as close as possible to the correct calibration curve for that specific sample.

Example 3

Qualitative Determination of Positive or Negative Cut-Off

The present invention enables a unique method for the establishment of a cut-off determination between positive and negative samples. Such a cut-off determination effectively establishes whether the result being generated by the assay is sufficiently reliable to be considered and reported. Normally, to establish a threshold cut-off of this type, samples that were negative for the analyte of interest were examined, and the level of reporter activity generated by such samples measured. A method was then used, usually the mean of the observations plus 3 to 5 standard deviations to set a cut-off between samples reported as negative (less than the mean+3 or 5 standard deviations) or positive (greater than the means+3 or 5 standard deviations). However, this method of determining a cut-off threshold does not work with homogeneous assays of the type utilized in the present invention.

Although anti-dsDNA antibody is often found in patients with Systemic Lupus Erythematosis (SLE), it is also often found at relatively low levels in healthy, asymptomatic individuals. The reason these low levels is not fully understood at this time. People skilled in the diagnosis of Lupus know that low levels of anti-dsDNA are not diagnostic for the disease. Therefore, it is important to establish a level of response that best discriminates between positive samples having clinically significant quantities of antibody, and negative samples that may possess some anti-dsDNA antibody, but not enough to be considered to be at clinically significant levels. People skilled in this diagnostic art consider levels of anti-dsDNA between 100 IU and 150 IU to be elevated, and more particularly, between 120 IU and 150 IU to have potential clinical significance.

FIG. 6 illustrates an enabling characteristic of the present invention. The inclusion of active calibrators, verifiers, and the method of data calculation used, enables the correct interpretation of raw fluorescence data that would be otherwise interpreted incorrectly. In the sample described in Example 2 hereabove, the fluorescence intensity (FI) observed for each dilution is shown, versus the IU of anti-DNA determined in the assay. The WHO standard has 200 IU of anti-dsDNA and the 1:2 dilution has 100 IU. Therefore, the level of antibody in the 1:2 dilution is a borderline positive result at best, and is actually considered "clinically negative" by many experts in the field. As shown in FIG. 6 however, FI alone cannot be used to correctly interpret the results of this sample. If a positive to negative FI cut-off were to be established, it would have to be lower than the level of FI obtained on the neat sample, because this sample is considered positive by experts throughout the world. However, for both the anti-dsDNA and the anti-RNP-A, the FI of the diluted sample was actually higher than that of the "neat" sample. These dilutions, therefore, would not only be incorrectly called positive based on FI, they would also be interpreted as having higher antibody levels than the neat sample. It is an important advantage of the present invention that the composition and method disclosed herein prevents such misinterpretations.

In practicing of the present invention, a cut-off may be set based upon the calculated IU obtained. In this manner, positive and negative samples are correctly interpreted base upon a cut-off threshold, the derived cut-off threshold, rather than the FI.

Example 4

Determining the Presence of Sample

An infrequent, but potentially dangerous source of error in many laboratory tests is a false negative result due to the failure to add sample. Such a failure can result from many types of errors including, but not limited to, instrument malfunction or human error by a laboratory professional. The present invention has a unique safeguard which prevents the reporting of false negative results due to the lack of sample. The active calibration system may be configured to require the sample to be present, intact, and of the appropriate type (serum instead of urine, for example) in order to function properly.

With the present method, four serum samples are diluted 1:200 in sample buffer solution for testing. Only sample buffer is placed in twenty additional wells. It is important to consider that no serum sample was added to any of these twenty additional wells. In all other aspects, the addition of reagents and all processing was the same for all tests performed in each well including all the wells that did received serum and those that did not. Ten microliters of sample were incubated with 50 microliters of microsphere suspension containing approximately 1000 microspheres of each of three calibrator subsets of microspheres along with one subset of calibration verifier microspheres. The binding capacity of the three different subsets of calibrator microspheres used were 12, 94, and 266 International Units (IU) respectively. The verifier microspheres had a predetermined value of 36 IU. The patient samples and calibrators and verifiers were incubated for 30 minutes at room temperature. At the end of the incubation time, 100 microliters of Goat anti-human IgG-PE was added to each well. The homogeneous suspension of sample and microspheres were incubated for an additional 30 minutes at room temperature, then the individually identifiable microspheres were read for tagging component on a dedicated flow cytometer, namely a Luminex 100 instrument from Luminex Corporation, Austin, Tex.

The table of FIG. 7 shows that the method of calibration used in accordance with the present invention, as well as the verification and data reduction process can accurately detect when sample has not been added to a given well. Where sample is missing, the slope of the curve falls to two or less. The intercept for wells without sample is not unlike what is seen when sample is present, and therefore is not a good indicator of whether that sample is actually present. The r-squared value for standard curves where the sample was not added is generally lower than 0.96, and often considerably lower. The value of the verifier was found to be the most sensitive indicator of the presence or absence of sample. Quality control checks may be employed by the user, or programmed into software that automatically calculates the standard curve and Value Ratio. In this way, samples where any or all of the slope, r-squared values, Verifier or Value Ratio values fall outside specified ranges may be flagged and results indicated as not being sufficiently reliable to be reported. This serves to greatly reduce the probability of reporting of a false, but believable negative result.

While particular embodiments of this invention have been shown in the drawings and described above, it will be apparent, that many changes may be made in the form, arrangement and positioning of the various elements of the combination. In consideration thereof it should be understood that preferred embodiments of this invention disclosed herein are intended to be illustrative only and not intended to limit the scope of the invention.

We claim:

1. A method for multiplexed homogeneous clinical immunoassay for detecting antibodies to specific antigens using microparticles for diagnostic purposes comprising:
   A. providing a multiplexed microparticle suspension having a plurality of individually identifiable subsets of microparticles having a diameter of at least approximately 1.0 microns and including a plurality of test subsets of microparticles each having a specific antigen positioned thereon which is capable of binding with a specific target antibody and including at least two calibration subsets of microparticles having a first binding partner thereon at known concentrations on each of said calibration subsets which is capable of binding with human antibodies and further including at least one verification subset of microparticles having a second binding partner thereon at a known concentration level;
   B. first mixing of the multiplexed suspension of microparticles with a human serum sample to allow binding of specific target antibodies to the specific antigens on each of said test subsets of microparticles and to facilitate binding of human antibodies to said first binding partners on said calibration subsets of microparticles;
   C. first incubating of the mixture of the human serum sample and the multiplexed microparticle suspension together;
   D. providing of a tagging component including an attaching component capable of binding with respect to human antibodies and with respect to the second binding partner and also including an indicating component conjugated with the attaching component which is capable of being detected;
   E. second mixing of the tagging component with the first incubated mixture of human serum sample and multiplexed microparticle suspension to facilitate binding of the tagging component with respect to antibodies which are bound to microparticles of the test subsets and calibration subsets and with respect to the second binding partner on the verification subset;
   F. second incubating of the tagging component with the first incubated mixture of human serum sample and the multiplexed microparticle suspension by maintaining thereof at a predefined temperature for a predefined period of time;
   G. measuring of the tagging component bound to microparticles of each test subset, calibration subset and verification subset of microparticles within the second incubated mixture;
   H. defining a mathematical algorithm expressing the mathematical relationship between the measured tagging component and the concentration level of antibody bound to each of the microparticles by measuring the tagging component found attached to microparticles of each of the calibration subsets thereof;
   I. verifying the defined mathematical algorithm by measuring the tagging component found on the verification subset of microparticles;
   J. measuring the amount of tagging component bound to each test subset of microparticles; and
   K. determining the concentration level of specific target antibodies within the human serum sample by applying the verified mathematical algorithm to the measured amount of tagging component bound to each test subset of microparticles.

2. The method for multiplexed homogeneous clinical immunoassay for detecting antibodies to specific antigens using microparticles for diagnostic purposes as defined in claim 1 wherein said defining a mathematical algorithm between the measured tagging component and the concentration level of antibody on the microparticles includes performing of a linear regression analysis on the measured amounts of tagging component found attached to each of the calibration subsets of microparticles in association with the known antibody concentrations thereon.

3. The method for multiplexed homogeneous clinical immunoassay for detecting antibodies to specific antigens using microparticles for diagnostic purposes as defined in claim 1 wherein said verifying of the defined mathematical algorithm includes:
   A. establishing a predicted value for the measured amount tagging component expected to be found attached to the verification subset of microparticles based on the defined mathematical algorithm;
   B. choosing maximum difference limits allowable between the predicted value and the actual value of tagging component measured attached to the verification subset of microparticles;

C. determining whether the measured value of tagging component attached to the verification subset of microparticles is within the chosen maximum difference limits;

D. if the measured value of the tagging component attached to the verification subset of microparticles is within the chosen maximum difference limits, then proceeding to measuring the amount of tagging component bound to each test subset of microparticles; and E. if the measured value of the tagging component attached to the verification subset of microparticles is not within the chosen maximum difference limits, then voiding of the immunoassay.

4. The method for multiplexed homogeneous clinical immunoassay for detecting antibodies to specific antigens using microparticles for diagnostic purposes as defined in claim 3 wherein, if the measured value of the tagging component is within the chosen maximum difference limits, then comparing the measured value of binding with the actual value of binding to yield a correction factor for the verification algorithm and applying of the correction factor to the mathematical algorithm therebetween prior to determining the concentration level of specific target antibodies within the human serum sample.

5. The method for multiplexed homogeneous clinical immunoassay for detecting antibodies to specific antigens using microparticles for diagnostic purposes as defined in claim 1 wherein said defining of a mathematical algorithm expresses a mathematically relationship between the amount of tagging component measured and the concentration level of antibody attached to the microparticles wherein the mathematical algorithm is a directly proportional.

6. The method for multiplexed homogeneous clinical immunoassay for detecting antibodies to specific antigens using microparticles for diagnostic purposes as defined in claim 1 wherein the first binding partner positioned on the calibration subsets of microparticles will bind with any immunoglobulin subclass such as type-G antibody found in human serum.

7. The method for multiplexed homogeneous clinical immunoassay for detecting antibodies to specific antigens using microparticles for diagnostic purposes as defined in claim 1 wherein said first incubating and said second incubating are each performed for a duration of approximately twenty to forty minutes at a temperature of approximately twenty to twenty-five degrees Centigrade.

8. The method for multiplexed homogeneous clinical immunoassay for detecting antibodies to specific antigens using microparticles for diagnostic purposes as defined in claim 1 wherein the test subsets of microparticles have specific antigens positioned thereon comprising are nuclear autoantigens capable of binding with specific target antibodies.

9. The method for multiplexed homogeneous clinical immunoassay for detecting antibodies to specific antigens using microparticles for diagnostic purposes as defined in claim 1 wherein each subset of microparticles includes approximately one thousand to five thousand individual microparticles, each having the same antigen positioned thereon capable of binding with the same antibody.

10. The method for multiplexed homogeneous clinical immunoassay for detecting antibodies to specific antigens using microparticles for diagnostic purposes as defined in claim 1 wherein said providing of the tagging component includes an indicating component which is fluorescent for facilitating measurement of the amount of tagging component bound to each microparticle.

11. The method for multiplexed homogeneous clinical immunoassay for detecting antibodies to specific antigens using microparticles for diagnostic purposes as defined in claim 1 wherein the calibration subsets are each provided with a first binding partner positioned thereon which comprises an anti-human antibody.

12. The method for multiplexed homogeneous clinical immunoassay for detecting antibodies to specific antigens using microparticles for diagnostic purposes as defined in claim 1 wherein the calibration subsets are each provided with a first binding partner positioned thereon which comprises an anti-human immunoglobulin type-G antibody.

13. The method for multiplexed homogeneous clinical immunoassay for detecting antibodies to specific antigens using microparticles for diagnostic purposes as defined in claim 1 wherein the calibration subsets are each provided with a first binding partner positioned thereon which comprises a goat antibody.

14. The method for multiplexed homogeneous clinical immunoassay for detecting antibodies to specific antigens using microparticles for diagnostic purposes as defined in claim 1 wherein the verification subset is provided with a second binding partner positioned thereon which comprises a human antibody.

15. The method for multiplexed homogeneous clinical immunoassay for detecting antibodies to specific antigens using microparticles for diagnostic purposes as defined in claim 1 wherein the verification subset is provided with a second binding partner positioned thereon which comprises a human immunoglobulin type-G antibody.

16. The method for multiplexed homogeneous clinical immunoassay for detecting antibodies to specific antigens using microparticles for diagnostic purposes as defined in claim 1 wherein the tagging component is provided with an attaching component comprising an anti-human immunoglobulin type-G antibody capable of binding to a human antibody and an indicating component comprising phycoerythrin conjugated to the attaching component which is capable of detection to facilitate detection of the presence and concentration of said tagging component and material bound with respect thereto, said indicating component being bound to said attaching component such that binding of the attaching component to human antibody will also attach said indicating component thereto in order to facilitate detection and measurement of human antibody present.

17. The method for multiplexed homogeneous clinical immunoassay for detecting antibodies to specific antigens using microparticles for diagnostic purposes as defined in claim 16 wherein the anti-human immunoglobulin type-G antibody is a goat antibody.

18. The method for multiplexed homogeneous clinical immunoassay for detecting antibodies to specific antigens using microparticles for diagnostic purposes as defined in claim 1 wherein the calibration subsets are provided with a first binding partner positioned thereon which has the same specific binding characteristics as the attaching component of the tagging component.

19. The method for multiplexed homogeneous clinical immunoassay for detecting antibodies to specific antigens using microparticles for diagnostic purposes as defined in claim 18 wherein the material of the first binding partner and the attaching component of the tagging component are both the same anti-human immunoglobulin antibody.

20. The method for multiplexed homogeneous clinical immunoassay for detecting antibodies to specific antigens using microparticles for diagnostic purposes as defined in claim 19 wherein the anti-human immunoglobulin type-G antibody in the first binding partner and of the tagging component each comprise goat antibody.

21. The method for multiplexed homogeneous clinical immunoassay for detecting antibodies to specific antigens using microparticles for diagnostic purposes as defined in claim 1 wherein the multiplexed suspension of microparticles are provided with three calibration subsets of microparticles wherein each subset thereof captures a different distinguishable concentration of the first binding partner positioned thereon to enhance accuracy of calibration of the immunoassay.

22. A method for multiplexed homogeneous clinical assay of a sample for detecting bound analytes to specific analyte binding partners using microparticles for diagnostic purposes comprising:
  A. providing a multiplexed microparticle suspension having a plurality of individually identifiable subsets of microparticles having a diameter of at least approximately 1.0 microns and including a plurality of test subsets of microparticles having a specific analyte binding partner positioned thereon which is capable of binding with specific target analytes and including at least two calibration subsets of microparticles having a first binding partner thereon at known different concentration levels on each calibration subset which is capable of binding with general analytes and further including at least one verification subset of microparticles having a second binding partner thereon at a known concentration level;
  B. first mixing of the multiplexed suspension of microparticles with the sample to allow binding of specific target analytes to the specific analyte binding partners on each of the test subsets of microparticles and to facilitate binding of general analytes to the first binding partners on the calibration subsets of microparticles;
  C. first incubating of the mixture of the sample and the multiplexed microparticle suspension together;
  D. providing of a tagging component including an attaching component capable of binding with respect to general analytes and with respect to said second binding partner and also including an indicating component conjugated with the attaching component which is capable of being detected;
  E. second mixing of the tagging component with the first incubated mixture of sample and multiplexed microparticle suspension to facilitate binding of the tagging component with respect to specific target analytes bound to microparticles of the test subsets and with respect to the general analytes bound to microparticles of the calibration subsets and to the second binding partner on the verification subsets thereof;
  F. second incubating of the tagging component with the first incubated mixture of sample and the multiplexed microparticle suspension by maintaining thereof at a predefined temperature for a predefined period of time;
  G. measuring of the tagging component bound to microparticles of each test subset, calibration subset and verification subset of microparticles within the second incubated mixture;
  H. defining a mathematical algorithm expressing the mathematical relationship between the measured tagging component and the concentration level of analyte bound to each of the microparticles by measuring the tagging component found attached to microparticles of each of the calibration subsets thereof;
  I. verifying the defined mathematical algorithm by measuring the tagging component found attached to the verification subset of microparticles;
  J. measuring the amount of tagging component bound to each test subset of microparticles; and
  K. determining the concentration level of specific target analytes within the sample by applying the verified mathematical algorithm to the measured amount of tagging component bound to each test subset of microparticles.

23. The method for multiplexed homogeneous clinical assay of a sample for detecting bound analytes to specific analyte binding partner using microparticles for diagnostic purposes as defined in claim 22 wherein the sample being tested is a human serum sample and wherein the analytes are human antibodies and wherein the analyte binding partners are antigens and wherein the first binding partner is a anti-human antibody and wherein the second binding partner is a human antibody.

* * * * *